(12) United States Patent
Ghanem et al.

(10) Patent No.: US 11,124,607 B2
(45) Date of Patent: Sep. 21, 2021

(54) DIAMINES, POLYIMIDES, METHODS OF MAKING EACH, AND METHODS OF USE

(71) Applicant: King Abdullah University of Science and Technology, Thuwal (SA)

(72) Inventors: Bader Saleh Ghanem, Thuwal (SA); Ingo Pinnau, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 203 days.

(21) Appl. No.: 16/304,421

(22) PCT Filed: Jun. 2, 2017

(86) PCT No.: PCT/IB2017/053284
§ 371 (c)(1),
(2) Date: Nov. 26, 2018

(87) PCT Pub. No.: WO2017/212382
PCT Pub. Date: Dec. 14, 2017

(65) Prior Publication Data
US 2019/0194393 A1    Jun. 27, 2019

Related U.S. Application Data

(60) Provisional application No. 62/346,591, filed on Jun. 7, 2016.

(51) Int. Cl.
| | | |
|---|---|---|
| *C08G 73/02* | (2006.01) | |
| *C08G 73/10* | (2006.01) | |
| *B01D 53/22* | (2006.01) | |
| *B01D 71/76* | (2006.01) | |
| *B01D 71/64* | (2006.01) | |
| *C07C 209/36* | (2006.01) | |
| *C07C 211/61* | (2006.01) | |

(52) U.S. Cl.
CPC ....... *C08G 73/0273* (2013.01); *B01D 53/228* (2013.01); *B01D 71/64* (2013.01); *B01D 71/76* (2013.01); *C07C 209/365* (2013.01); *C07C 211/61* (2013.01); *C08G 73/1053* (2013.01); *C08G 73/1064* (2013.01); *C08G 73/1082* (2013.01); *Y02P 20/129* (2015.11)

(58) Field of Classification Search
CPC ...... B01D 53/228; B01D 71/64; B01D 71/76; C08G 73/0273; C08G 73/1053; C08G 73/1064; C08G 73/1067; C08G 73/1078; C08G 73/1082; C07C 209/365; C07C 211/61
See application file for complete search history.

(56) References Cited

U.S. PATENT DOCUMENTS

2016/0367948 A1* 12/2016 Song ............... B01D 53/228

FOREIGN PATENT DOCUMENTS

| WO | 2012035327 A1 | 3/2012 | |
|---|---|---|---|
| WO | WO 2014/207559 A2 * | 12/2014 | ........... B01D 53/228 |
| WO | 2015015299 A1 | 2/2015 | |
| WO | WO 2015/015299 A1 * | 2/2015 | ............. B01D 53/22 |

OTHER PUBLICATIONS

Carta, Mariolono et all., "Heterogeneous organocatalysts composed of microporous polymer networks assembled by Troger's base formation", Polymer Chemistry, 5, 2014, pp. 5262-5266. (Year: 2014).*
Cho, Yoon Jin et al., "High Performance Polyimide with High Internal Free Volume Elements", Macromolecular Rapid Communications, 32, 2011, pp. 579-586. (Year: 2011).*
Ghanem, Bader S., "A facile synthesis of novel triptycene-containing A-B monomer: precursor to polymers of intrinsic microporosity", Polymer Chemistry, 3, 2012, pp. 96-98. (Year: 2012).*
Carta, Mariolino et al., "Triptycene Induced Enhancement of Membrane Gas Selectivity for Microporous Troger's Base Polymers", Advanced Materials, 26, 2014, pp. 3526-3531. (Year: 2014).*
Search Report and Written Opinion for PCT/IB2017/053284 dated Sep. 21, 2017.
Carta, et al., "Heterogeneous organocatalysts composed of microporous polymer networks assembled by Troger's base formation", Royal Society of Polymer Chemistry, 5,, 2014.
Carta, et al., "Microporous polymer networks for heterogeneous organocatalysis assembled by Troger's base formation", Jun. 20, 2014.

* cited by examiner

*Primary Examiner* — Jason M Greene
(74) *Attorney, Agent, or Firm* — Billion & Armitage

(57) ABSTRACT

Aspects of the present disclosure provide for bridgehead-substituted triptycene-based diamines and methods of making bridgehead-substituted triptycene-based diamines.

15 Claims, No Drawings

DIAMINES, POLYIMIDES, METHODS OF MAKING EACH, AND METHODS OF USE

CROSS-REFERENCE TO RELATED APPLICATIONS

This application claims the benefit of and priority to U.S. Provisional Application Ser. No. 62/346,591, having the title "DIAMINES, POLYIMIDES, METHODS OF MAKING EACH, AND METHODS OF USE," filed on Jun. 7, 2016, the disclosure of which is incorporated herein in by reference in its entirety.

BACKGROUND

During the last decade high-free-volume glassy polymers of intrinsic microporosity (PIMs) have been developed and extensively studied. PIMs combine high internal surface areas with the design flexibility that can potentially be exploited in a number of important industrial applications including catalysis, selective adsorption of small molecules, sensors for trace substance detection, gas storage, and membrane-based separations. The microporosity in these materials is due to their rigid and contorted macromolecular architectures that pack inefficiently in the solid state. However, there is still a quest for novel custom-designed building blocks to further modify and develop new PIMs to further enhance their desirable properties and applications.

SUMMARY

Aspects of the present disclosure provide for bridgehead-substituted triptycene-based diamines and methods of making bridgehead-substituted triptycene-based diamines. In addition, embodiments of the present disclosure provide for polyimides and Tröger's base (TB) ladder type polymers made from bridgehead-substituted triptycene-based diamines.

In an aspect, the present disclosure includes a composition, among others, that includes: a monomer having the following structure:

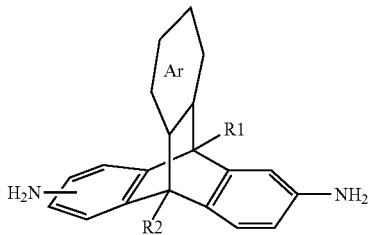

wherein Ar is a substituted or unsubstituted aromatic moiety, wherein R1 and R2 are independently an aryl group, a linear or branched alkyl group, a halogen, or a nitrile group, each of which can be substituted or unsubstituted.

In an aspect, the present disclosure includes a method of making a monomer, among others, that includes:

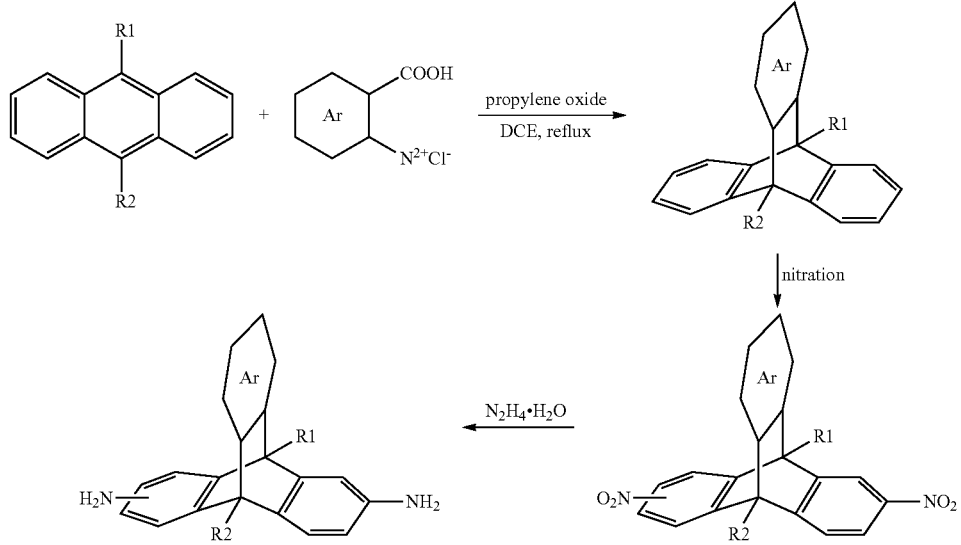

wherein Ar is a substituted or unsubstituted aromatic moiety, wherein R1 and R2 are independently an aryl group, a linear or branched alkyl group, a halogen, or a nitrile group, each of which can be substituted or unsubstituted.

In an aspect, the present disclosure includes a composition, among others, that includes: a polymer having the following structure:

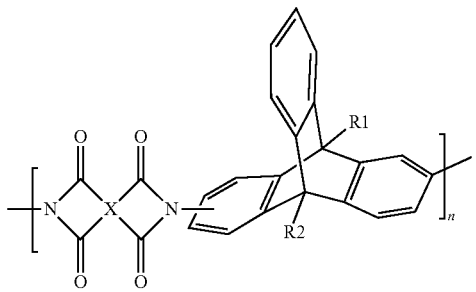

wherein X is a tetravalent radical having an aromatic or aliphatic ring, wherein each of R1 and R2 can independently be selected from an aryl group, a linear or branched, alkyl group, a halogen or a nitrile group, and wherein n is 1 to 10,000.

In an aspect, the present disclosure includes a composition, among others, that includes: a polymer having the following structure:

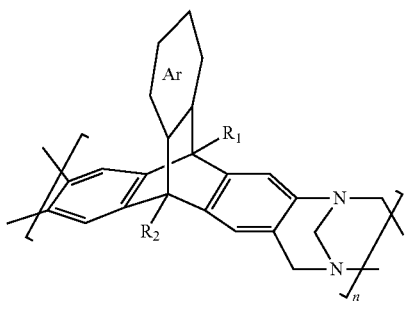

wherein Ar is a substituted or unsubstituted aromatic moiety, wherein R1 and R2 are independently an aryl group, a linear or branched, alkyl group, a halogen or a nitrile group, each of which can be substituted or unsubstituted, and wherein n is 1 to 10,000. In an embodiment, a membrane can be formed of the polymer. In an embodiment, the membrane can be used in a gas separation system.

In an aspect, the present disclosure includes a method of separating a mixture, among others, that includes: introducing a fluid mixture a membrane described herein, wherein the mixture includes a first component and a second component and the first component and the second component are different; and separating a first fluid component from the second fluid component when a first component passes through the membrane and the second component does not substantially pass through the membrane.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, polymer chemistry, analytical chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

The term "substituted" refers to any one or more hydrogens on the designated atom that can be replaced with a selection from the indicated group, provided that the designated atom's normal valence is not exceeded. In an aspect, substituted group may contain in place of one or more hydrogens a group such as alkyl, hydroxy, amino, halo, trifluoromethyl, cyano, —NH(lower alkyl), —N(lower alkyl)$_2$, lower alkoxy, lower alkylthio, or carboxy. In particular, the substituted group can be a halogen.

As used herein, "aliphatic" or "aliphatic group" refers to a saturated or unsaturated, linear or branched, cyclic (non-aromatic) or heterocyclic (non-aromatic), hydrocarbon or hydrocarbon group and encompasses alkyl, alkenyl, and alkynyl groups, and alkanes, alkene, and alkynes, for example. Reference to aliphatic includes substituted or unsubstituted.

As used herein, "cyclic" group refers to a cyclic hydrocarbon having a stable 4, 5, 6, 7, 8, 9, 10, 11, or 12 membered (e.g., carbon or hetero), (unless the number of members is otherwise recited), monocyclic, bicyclic, or tricyclic cyclic ring. Reference to cyclic includes substituted or unsubstituted.

As used herein, "alkyl" or "alkyl group" refers to a linear or branched saturated aliphatic hydrocarbon (e.g., 1 to 20 carbons, 1 to 10 carbons, or 1 to 6 carbons), that can be saturated or unsaturated. Examples of alkyl include, but are not limited to iso-propyl, sec-butyl, t-butyl, and iso-pentyl. Reference to alkyl includes substituted or unsubstituted.

The term "substituted," as in "substituted alkyl", "substituted aryl," "substituted heteroaryl" and the like means that the substituted group may contain in place of one or more hydrogens a group such as alkyl, hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "aryl" as used herein, refers to an aromatic monocyclic or multicyclic ring system of about 4 to about 14 carbon atoms, preferably of about 6 to about 10 carbon atoms, where one or more hydrocarbons from the aromatic hydrocarbon are replaced to form one or more bonds, for example a bond can be formed from two carbons by the removal of a hydrocarbon from two carbons of the aromatic hydrocarbon. Exemplary aryl groups include phenyl or naphthyl, or phenyl substituted or naphthyl substituted. Reference to aryl includes substituted or unsubstituted.

The term "heteroaryl" is used herein to denote an aromatic ring or fused ring structure of carbon atoms (e.g., 4 to 14) with one or more non-carbon atoms (e.g., 1 to 6), such as oxygen, nitrogen, and sulfur, in the ring or in one or more of the rings in fused ring structures. Preferred examples are furanyl, imidazyl, pyranyl, pyrrolyl, and pyridyl. Reference to heteroaryl includes substituted or unsubstituted.

General Discussion

Aspects of the present disclosure provide for bridgehead-substituted triptycene-based diamines and methods of making bridgehead-substituted triptycene-based diamines. In addition, embodiments of the present disclosure provide for polyimides and Tröger's base (TB) ladder type polymers made from bridgehead-substituted triptycene-based diamines. Due to their good solubilities, thermal and chemical stabilities, and/or high microporosities, these materials can be implemented in a wide range of industrial applications related to aerospace industry, electronic industry, high temperature adhesion, membranes for separation, composite materials, sensors for trace substance detection, and in high temperature adhesion and composite mate.

In an embodiment, the polyimides and/or the TB ladder type polymers can be used to make membranes. In an embodiment, the membranes of the present disclosure can be used in membrane-based gas separation applications (e.g., a gas separation system) including air separation for oxygen ($O_2/N_2$), nitrogen enrichment, hydrogen recovery ($H_2/N_2$ and $H_2/C_4$), natural gas sweetening ($CO_2/CH_4$), and carbon capture from flue gas ($CO_2/N_2$) as well as acid gas removal and hydrocarbon recovery from natural gas streams.

Embodiments of the present disclosure have one or more of the following characteristics: intrinsic microporosity, good thermal stability, and enhanced solubility. Intrinsic microporosity is defined herein as a polymeric material with pore sizes of less than 2 nm and a surface porosity of >100 $m^2/g$, as determined by the nitrogen adsorption method at 77 K.

Embodiments of the present disclosure describe an efficient approach for the synthesis of bridgehead-substituted diamino triptycene monomers (e.g., bridgehead-substituted 2,6(7)-diamino triptycene monomers). In addition, embodiments of the present disclosure provide for using bridgehead-substituted diamino triptycene monomers in the synthesis of high performance microporous materials. The bridgehead substituents can be selected to fine-tune the resulting polymers structural properties such as rigidity and free volume, which in turn will affect their properties and applications.

The scheme below illustrates an embodiment of a method of forming the bridgehead-substituted triptycene-based diamine.

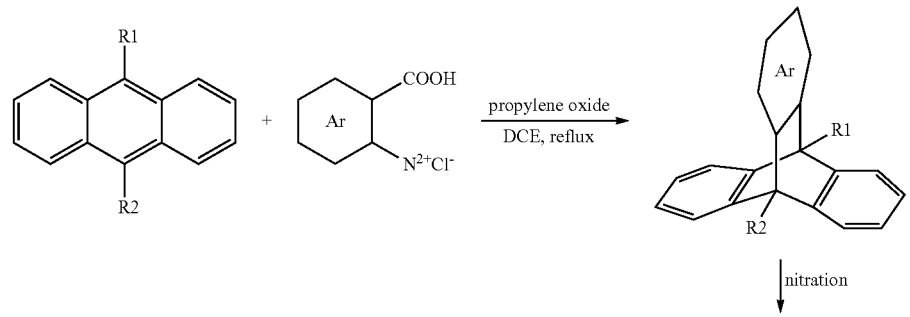

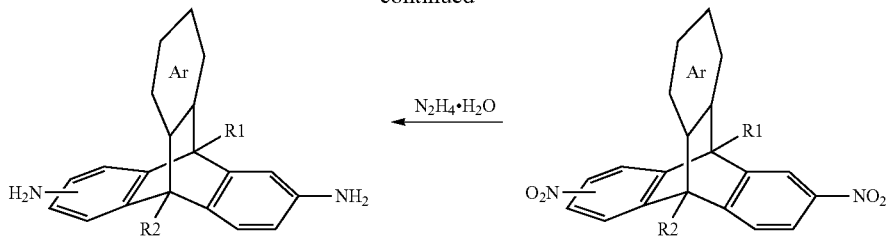

In an embodiment, Ar can be a substituted or unsubstituted aromatic moiety (e.g., although 6 carbons are shown the ring can be 4 to 8 carbons), which can be substituted or unsubstituted. In an embodiment, the aromatic moiety can be: an aryl group or a heteroaryl group (each having two carbons that form bonds to the remaining portion of the compound such as shown in the scheme), where each can be substituted or unsubstituted.

In an embodiment, each of R1 and R2 can independently be selected from an aryl group, a linear or branched, alkyl group, a halogen or a nitrile group, each of which can be substituted or unsubstituted. In an embodiment, each of R1 and R2 can independently be H. In an embodiment, R1 and R2 are the same, while in other embodiments, R1 and R2 are different.

In an embodiment, the bridgehead-substituted triptycene-based diamine can be synthesized via a three-step synthetic route (see above). The parent compound, 9,10-disubstituted triptycene was prepared by the conventional Diels-Alder reaction of the benzyne (obtained by the reaction of 2-amino benzoic acid with isoamyl nitrite) with the appropriate anthracene. Nitration of the 9,10-disubstituted triptycene followed by the reduction of the dinitro groups yield the desired 9,10-disubstituted-2,6(7)-diaminotriptycene monomers. In an embodiment, the molecular structures of all products and the two diamines were confirmed by $^1$H and $^{13}$C NMR, FTIR and mass spectroscopic analysis.

Polyimides (PIs) and Tröger's base (TB) ladder type polymers are two of the types of intrinsically microporous polymers that can be obtained from the bridgehead-substituted triptycene-based diamine of the present disclosure (shown below).

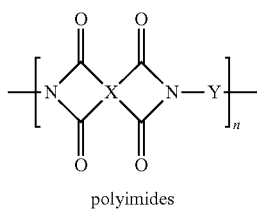

a)

polyimides

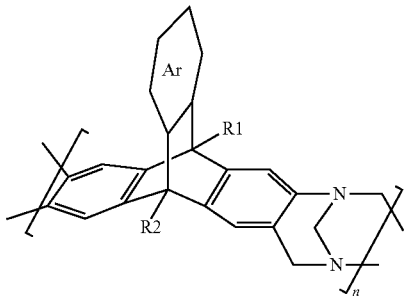

Tröger's base polymers b)

In an embodiment, X can be a tetravalent radical having an aromatic or aliphatic ring. In an embodiment, n can be from 2 to 10,000. In an embodiment, each of $R_1$ and $R_2$ (in b) above) can independently be selected from H or an aryl group, a linear or branched, alkyl group, a halogen or a nitrile group, each of which can be substituted or unsubstituted. In an embodiment, $R_1$ and $R_2$ are the same, while in other embodiments, $R_1$ and $R_2$ are different.

In an embodiment, X can include one of the following structures:

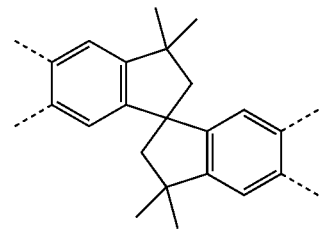

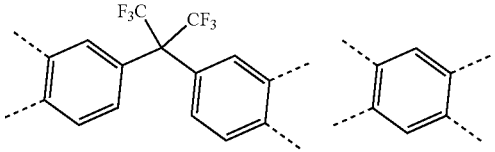

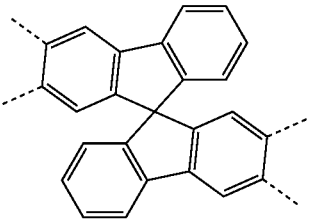

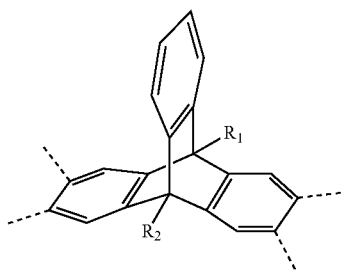

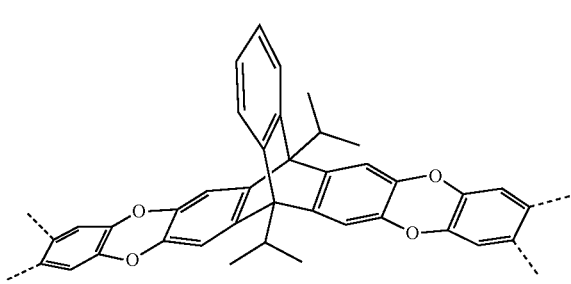

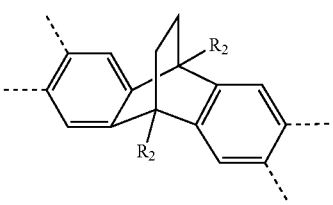

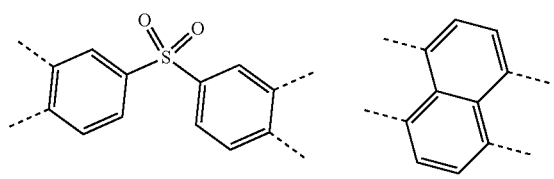

In an embodiment, each $R_1$ and $R_2$ (as used for the structures of X) can be independently selected from: a halogen and an alkyl group. In an embodiment, each $R_1$ and $R_2$ (as used for the structures of X) can be H. In an aspect when the bond is directed to the middle of a ring, this indicates that, optionally, 1 to 4 R groups can be attached to the ring and each R group is independently selected. In an embodiment, $Ar_1$ can be selected from: an aryl group and a heteroaryl group, where each are substituted or unsubstituted.

As used herein, the phrase "independently selected from" can mean selection from $R_1$ and $R_2$ independent of one another, or can mean that in each instance of $R_1$ (as well as $R_2$), each $R_1$ is selected independently of the other $R_1$s (e.g., one $R_1$ can be a methyl group and the other $R_1$ can be a propyl group).

In an embodiment, Y can be a divalent organic group presented by formula (1) below, where $R_1$, $R_2$, and Ar correspond to the same groups on the bridgehead-substituted triptycene-based diamine.

Formula (1)

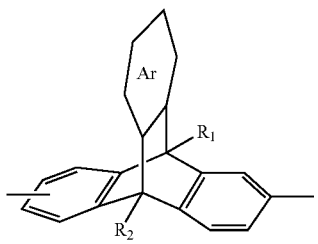

In an aspect, the present disclosure includes a composition, among others, that includes: a polymer having the following structure (n=1 to 10,000):

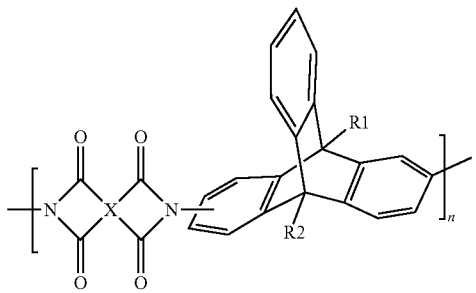

In an embodiment, the aromatic polyimides can be obtained via the high-temperature polycondensation reaction between equimolar amounts of tetracarboxylic dianhydride monomers and 9,10-dimethyl-2,6(7)-diaminotriptycene monomer in m-cresol containing catalytic amount of isoquinoline (a shown above). The preferred dianhydride monomers could be, but are not restricted to, the following: 4'-hexafluoroisopropylidene diphthalic anhydride (6FDA), triptycene tetracarboxylic dianhydride (TDA and TPDA), naphthalenetetracarboxylic dianhydride (NTDA), 3,3',4,4'-diphenylsulfonetetracarboxylic dianhydride, and bicyclo[2.2.2]oct-7-ene-2,3,5,6-tetracarboxylic dianhydride (BTDA). These tetracarboxylic dianhydrides can be used singly or in combination (copolymers).

In an embodiment, Tröger's base ladder-type polymer can be obtained via the acid-catalyzed condensation of the 9,10-disubstituted-2,6(7)-diamino triptycene with dimethoxymethane (DMM), (b shown above).

Illustrative embodiments of the present disclosure can include:
PI-1
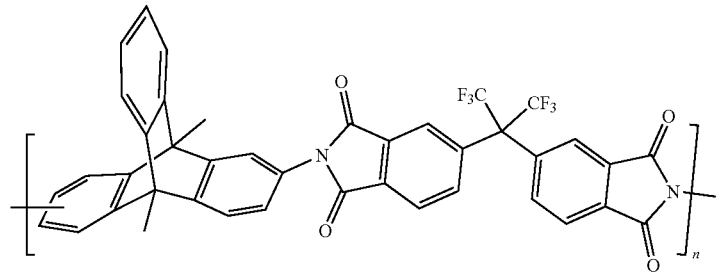
PI-2
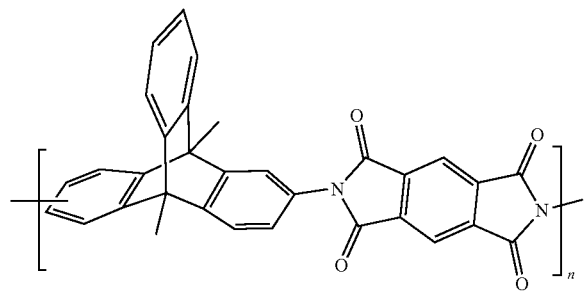
PI-3
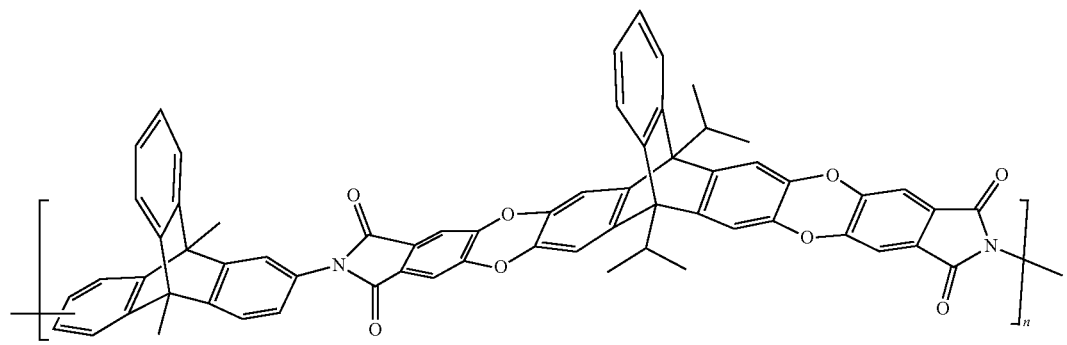
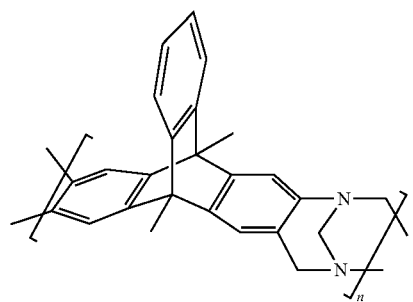
TB-ladder polymer-1
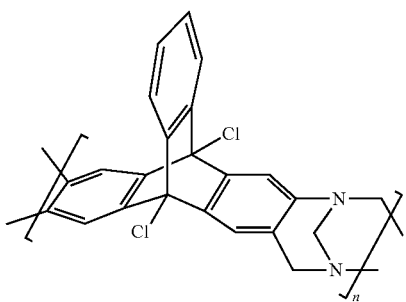
TB-ladder polymer-2

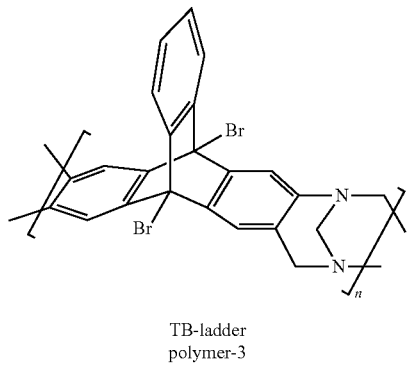

TB-ladder
polymer-3

As mentioned above, a membrane including one or more of the polymer described herein. Embodiments of the membranes can be used in gas separation, nanofiltration, pervaporation and the like, as well as sensor applications. The membrane can be used to separate mixtures such as gas mixtures. Exemplary embodiments of mixtures includes the following: $O_2/N_2$; $H_2/N_2$; $H_2/C_{1+}$ hydrocarbon; $He/C_{1+}$ hydrocarbon; $CO_2/C_{1+}$ hydrocarbons; $CO_2/N_2$; $CH_4/H_2S$; and olefin/paraffin. In an embodiment, the membrane can have a thickness one the scale of microns to centimeters or more, depending upon the particular application. The polymers of the present disclosure can be fabricated into any type of membrane structure.

Embodiments of the present disclosure provide for methods of separating a fluid mixture (e.g., a gas mixture). A mixture can be introduced to a membrane that includes the polymer(s) described herein. The mixture includes a first component and a second component and the first component and the second component are different. The mixture can be a gas or liquid. The mixture can include those described herein. A first component can be separated from the second component when a first component passes through the membrane and the second component does not substantially (e.g., less than about 20%, less than about 10%, less than about 5%, less than about 2%, less than about 1%, less than about 0.5%) pass through the membrane or does not pass through the membrane.

EXAMPLES

Now having described the embodiments of the disclosure, in general, the examples describe some additional embodiments. While embodiments of the present disclosure are described in connection with the example and the corresponding text, there is no intent to limit embodiments of the disclosure to these descriptions. On the contrary, the intent is to cover all alternatives, modifications, and equivalents included within the spirit and scope of embodiments of the present disclosure.

Example 1

Synthesis of 2,6(7)-diamino-9,10-dimethyltriptycene (DMDAT)

a) Synthesis of 9,10-dimethyltriptycene (DMT)

Concentrated HCl (8.8 ml) and isoamyl nitrite (22 ml) were added to an ice-cooled solution of anthranilic acid (12 g, 28.80 mmol) in ethanol (130 ml). After stirring for 15 minutes, diethyl ether (130 ml) was added and the reaction mixture was stirred for further 15 minutes. The resulting precipitate was filtered, washed with ether and dried using a vacuum aspirator and directly added to a hot solution of 9,10-dimethylanthracene (5.2 g, 25.2 mmol), in dichloroethane (170 ml) and 1,2-epoxypropane (20 ml). After refluxing for 5 h, the solvent was removed under vacuum and the residual solid was filtered and washed with methanol to give white crystals (6.45 g, 91% yield). $^1$H NMR (400 MHz, $CDCl_3$, δ): 2.44 (s, 6H), 7.05 (m, 6H), 7.38 (m, 6H).

b) Synthesis of 9,10-dimethyl-2,6(7)-dinitrotriptycene (DMDNT)

Trifluoroacetic anhydride (21 g, 99.67 mmol) was added slowly to a stirred mixture of 9,10-dimethyltriptycene (4.02 g, 14.24 mmol), potassium nitrate (2.95 g, 29.19 mmol) and acetonitrile (150 ml. After stirring at room temperature for 20 h, the mixture was added to 500 ml water and the resulting white solid was filtered and washed with water and methanol. The crude product was purified by column chromatography over silica gel with hexane/DCM 1:1 as eluent to give the dinitro product (4.37 g, 82% yield). $^1$H NMR (400 MHz, $CDCl_3$, δ): 2.53 (t, 6H), 7.13-7.15 (m, 2H), 7.41-7.46 (m, 2H), 7.49-7.52 (m, 2H), 7.98 (dd, 2H), 8.20 (t, 2H). FTIR (powder, v, $cm^{-1}$): 1516, 1337 (symmetic and asymmetric-$NO_2$ streching), 849 (C—N streching for aromatic —$NO_2$).

c) Synthesis of 9,10-dimethyl 2,6(7)-diaminotriptycene (DMDAT)

To a stirred mixture of 9,10-dimethyl-2,6(7)-dinitrotriptycene (6.0 g, 16.11 mmol) and palladium/carbon 10% (3 g) in absolute ethanol (180 ml), was added hydrazine monohydrate (22.8 ml, 725.73 mmol). After refluxing for 6 h under a $N_2$ atmosphere, the mixture was filtered and added to stirred distilled water (500 ml). The resulting white solid was collected and dried under vacuum at 100° C. for 20 h to give the diamine monomer in 88% yield. $^1$H NMR (DMSO-$d_6$, δ): 2.13 (s, 6H), 4.84 (s, 4H), 6.12-6.16 (m, 2H), 6.60 (dd, 2H), 6.89-6.93 (m, 2H), 6.96-6.98 (m, 2H), 7.21-7.27 (m, 2H). HRMS(ESI): (m/z) calc. for $C_{22}H_{20}N_2$: 312.1626; Found 313.1699 [M+H]$^+$. FTIR (powder, v, $cm^{-1}$): 3439, 3360 (N—H streching), 3014 (aromatic C—H streching), 2878-2970 (aliphatic C—H streching).

Example 2

Synthesis of 9,10-dichloro-2,6(7)-diaminotriptycene (DCDAT)

a) Synthesis of 9,10-dichlorotriptycene (DCT)

Concentrated HCl (10.1 ml) and isoamyl nitrite (25.2 ml) were added to an ice-cooled solution of anthranilic acid (13.6 g, 99.17 mmol) in ethanol (130 ml). After stirring for 15 minutes, diethyl ether (130 ml) was added and the reaction mixture was stirred for further 15 minutes. The resulting precipitate was filtered, washed with ether and dried under vacuum and then directly added to a hot solution of 9,10-dichloroanthracene (5.0 g, 20.23 mmol) in dichloroethane (150 ml) and 1,2-epoxypropane (20 ml). After refluxing for 5 h, the solvent was removed under vacuum and the residual solid was filtered and washed with methanol to give white crystals (4.54 g, 69% yield). $^1$H NMR (400 MHz, CDCl$_3$, δ): 7.10-7.13 (m, 6H), 7.73-7.77 (m, 6H). $^{13}$C NMR (100 MHz, CDCl$_3$, δ): 73.8, 121.3, 126.47, 142.8. FTIR (powder, ν, cm$^{-1}$): 1440, 1599 (C=C str.), 2852-2922 (C—H str. aliphatic), 3027-3066 (C—H str. aromatic).

b) Synthesis of 9,10-dichloro-2,6(7)-dinitrotriptycene (DCDNT)

A mixture of DCT (2.0 g, 6.19 mmol), cerium ammonium nitrate (CAN) (6.8 g, 12.47 mmol), dichloromethane (40 ml) and sulfuric acid (1.8 ml) was stirred at room temperature for two days. The mixture was added to excess water and extracted with dichloromethane, basified with potassium carbonate and dried over magnesium sulfate. The crude product was purified by column chromatography over silica gel with hexane/DCM (3:1) as eluent to give the dinitro product (1.93 g, 75% yield). $^1$H NMR (400 MHz, CDCl$_3$, δ): 7.26-7.30 (m, 2H), 7.82-7.85 (m, 2H), 7.96-7.98 (m, 2H), 8.211-8.13 (m, 2H), 8.62-8.36 (m, 2H). $^{13}$C NMR (100 MHz, CDCl$_3$, δ): 72.3, 72.6, 73, 117.3, 117.4, 122, 122.1, 122.2, 123.9, 123, 123.1, 127.8, 139.9, 140.2, 140.6, 143.8, 144.1, 146.9, 147.7, 148. FTIR (powder, ν, cm$^{-1}$): 1524, 1339 (symmetic and asymmetric-NO$_2$ streching), 828 (C—N streching for aromatic —NO$_2$), 2851-2923 (C—H str. aliphatic), 3026-3102 (C—H str. aromatic).

c) Synthesis of 9,10-dichloro-2,6(7)-diaminotriptycene (DCDAT)

To a stirred mixture of DCDNT (0.55 g, 1.33 mmol) and palladium/carbon 10% (0.078 g) in absolute ethanol (26 ml), was added hydrazine monohydrate (1.54 ml, 49.02 mmol). After refluxing for 2 h under N$_2$ atmosphere, the mixture was filtered and added to stirred distilled water (500 ml). The resulting white solid was collected and dried under vacuum at 100° C. for 20 h to give the diamine monomer in 84% yield. $^1$H NMR (DMSO-d$_6$,δ): 5.33 (s, 4H), 6.28-6.31 (m, 2H), 6.97 (dd, 2H), 7.18-7.21 (m, 2H), 7.24-7.28 (m, 2H), 7.59-7.65 (m, 2H).

Example 3

Synthesis of 9,10-dibromo-2,6(7)-diaminotriptycene (DBDAT)

a) Synthesis of 9,10-dibromotriptycene (DBT)

Concentrated HCl (7.4 ml) and isoamyl nitrite (18.5 ml) were added to an ice-cooled solution of anthranilic acid (10 g, 72.92 mmol) in ethanol (100 ml). After stirring for 15 minutes, diethyl ether (100 ml) was added and the reaction mixture was stirred for further 15 minutes. The resulting precipitate was filtered, washed with ether and dried under vacuum aspirator and directly added to a hot solution of 9,10-dibromoanthracene (5.0 g, 14.88 mmol), in dichloroethane (170 ml) and 1,2-epoxypropane (25 ml). After refluxing for 6 h, the solvent was removed under vacuum and the residual solid was purified by column chromatography over silica gel with petroleum ether as eluent to give the dinitro product (4.94 g, 81% yield). $^1$H NMR (400 MHz, CDCl$_3$, δ): 7.08-7.10 (m, 6H), 7.8-7.81 (m, 6H). $^{13}$C NMR (100 MHz, CDCl$_3$, δ): 70.91, 123.53, 126.69, 142.91. FTIR (powder, ν, cm$^{-1}$): 1439, 1600 (C=C str.), 2849-2923 (C—H str. aliphatic), 3002-3079 (C—H str. aromatic).

b). Synthesis of 9,10-dibromo-2,6(7)-dinitrotriptycene (DBDNT)

A mixture of DBT (1.25 g, 3.03 mmol), cerium ammonium nitrate (CAN) (3.3 g, 6.05 mmol), dichloromethane (25 ml) and sulfuric acid (0.8 ml) was stirred at room temperature for two days. The mixture was added to excess water and extracted with dichloromethane, basified with potassium carbonate and dried over magnesium sulfate. The crude product was purified by column chromatography over silica gel with petroleum ether/DCM (5:1) as eluent to give the dinitro product (1.08 g, 71% yield). $^1$H NMR (400 MHz, CDCl$_3$, δ): 7.36-7.37 (m, 2H), 7.87-7.89 (m, 2H), 8.10-8.11 (m, 2H), 8.18-8.20 (m, 2H), 8.51-8.52 (m, 2H). $^{13}$C NMR (100 MHz, CDCl$_3$, δ): 67.0, 67.4, 67.7, 118.5, 118.7, 123.8, 124.0, 124.2, 124.3, 125.6, 125.7, 128.4, 140.0, 140.2, 140.5, 143.1, 143.4, 146.7, 147.3, 147.6. FTIR (powder, ν, cm$^{-1}$): 1522, 1339 (symmetic and asymmetric-NO$_2$ streching), 829 (C—N streching for aromatic —NO$_2$), 2852-2923 (C—H str. aliphatic), 3027-3093 (C—H str. aromatic).

c) Synthesis of 9,10-dibromo-2,6(7)-diaminotriptycene (DBDAT)

To a stirred mixture of 9,10-dibromo-2,6(7)-dinitrotriptycene DBDNT (1.14 g, 2.27 mmol) and palladium/carbon 10% (0.12 g) in absolute ethanol (55 ml), was added hydrazine monohydrate (2.6 ml, 82.76 mmol). After refluxing for 2 minutes under a N$_2$ atmosphere, the mixture was filtered and added to stirred distilled water (300 ml). The resulting white solid was collected and dried under vacuum at 100° C. for 20 h to give the diamine monomer in 80% yield. $^1$H NMR (DMSO-d$_6$,δ): 5.34 (s, 4H), 6.30-6.33 (m, 2H), 6.98-7.02 (dd, 2H), 7.18-7.20 (m, 2H), 7.27-7.31 (t, 2H), 7.60-7.67 (m, 2H). $^{13}$C NMR (100 MHz, CDCl$_3$, δ): 73.3, 73.8, 74.4, 107.2, 107.7, 109.6, 109.9, 119.7, 120.2, 120.7, 121.2, 121.7, 126, 126.4, 126.7, 129.6, 130.6, 142.8, 143.1, 143.5, 143.9, 144.3, 147.5, 147.7. FTIR (powder, ν, cm$^{-1}$): 3451, 3205, 3358 (N—H streching), 3027-3062 (aromatic C—H streching), 2851-2922 (aliphatic C—H streching).

Synthesis of the Polyimides 1-3 (Typical Procedure)

To a dry 10 mL Schlenk tube were added 9,10-dimethyl-2,6-diaminotriptycene (1 mmol) and freshly distilled m-cresol (4 ml). After stirring for 5 min under a flow of nitrogen, an equimolar amount of the dianhydride (1.0 mmol) and catalytic amount of isoquinoline were added. The mixture was stirred at ambient temperature for 15 minutes and then the temperature was raised gradually to 200° C. and kept at that temperature for about 3 h. During this period water formed by the imidization reaction was removed by a stream of nitrogen. After cooling to 50° C., the polymer solution was added into excess methanol. The resulting polymer precipitate was collected and reprecipitated twice from appropriate solvent into methanol and then dried under vacuum at 120° C. for 20 h.

Example 4

Synthesis of PI-1

Following the above typical procedure polyimide 1 was prepared from 6FDA and 9,10-dimethyl-2,6(7)-diaminotriptycene as an off-white powder in 89% yield after reprecipitation twice from chloroform into methanol. $^1$H-NMR (400

MHz, CDCl$_3$) δ (ppm): 2.43 (t, 6H), 7.09 (m, 4H), 7.38 (m, 4H), 7.50 (d, 2H), 7.83 (m, 2H), 7.87 (s, 2H), 7.97 (m, 2H). FT-IR (membrane, ν, cm$^{-1}$): 1783 (asym C=O, str), 1720 (sym C=O, str), 1365 (C—N, str), 847 (imide ring deformation). Analysis by GPC (CHCl$_3$): M$_n$=118,300 g mol$^{-1}$, M$_w$=192,300 g mol$^{-1}$ relative to polystyrene, M$_w$/M$_n$=1.63. BET surface area=395 m$^2$ g$^{-1}$. TGA analysis: (N$_2$), initial weight loss due to thermal degradation commences at T$_d$=530° C.

Example 5

Synthesis of PI-2

Following the above typical procedure polyimide 2 was prepared from PMDA and 9,10-dimethyl-2,6(7)-diaminotriptycene as an off-white powder in quantitative yield after reprecipitation twice from dimethylacetamide into methanol. FT-IR (membrane, ν, cm$^{-1}$): 1776 (asym C=O, str), 1716 (sym C=O, str), 1354 (C—N, str), 831 (imide ring deformation) BET surface area=402 m$^2$ g$^{-1}$. TGA analysis: (N$_2$), initial weight loss due to thermal degradation commences at T$_d$=590° C.

Example 6

Synthesis of PI-3

Following the above typical procedure polyimide 3 was prepared from TPDA and 9,10-dimethyl-2,6(7)-diaminotriptycene as yellow powder in 96% yield after reprecipitation twice from chloroform into methanol. $^1$H-NMR (400 MHz, CDCl$_3$) δ (ppm): 1.78-1.87 (br m, 12H), 2.4 (br m, 6H), 3.29-3.49 (m, 2H), 6.90-7.05 (m, 8H), 7.23-7.45 (m, 14H). FT-IR (membrane, ν, cm$^{-1}$): 1778 (asym C=O, str), 1718 (sym C=O, str), 1349 (C—N, str), 859 (imide ring deformation). Analysis by GPC (CHCl$_3$): M$_n$=286,000 g mol$^{-1}$, M$_w$=456,000 g mol$^{-1}$ relative to polystyrene, M$_w$/M$_n$=1.59. BET surface area=640 m$^2$ g$^{-1}$. TGA analysis: (N$_2$), initial weight loss due to thermal degradation commences at T$_d$=510° C.

Synthesis of Triptycene-Based Tröger's Base Ladder Polymers (Typical Procedure)

2,6(7)-diaminotriptycene (1.6 mmol) was stirred with dimethoxymethane (0.70 mL, 8 mmol) at 0° C. Trifluoracetic acid (5 ml) was added dropwise over a period of 15 minutes, and the solution was stirred vigorously under nitrogen atmosphere for 20 h at room temperature. The highly viscous orange solution was quenched with ammonium hydroxide solution (20%, 100 ml) and stirred vigorously for 10 h. The resulting polymer was filtered, washed with water and purified by reprecipitation from chloroform/methanol mixture twice and then dried under vacuum at 130° C. to give the desired product as pale yellow powder.

Example 7

Synthesis of Tröger's Base Ladder Polymer 1 (TB-1)

Following the above typical procedure, TB-1 was prepared from 9,10-dimethyl-2,6(7)-diaminotriptycene as pale yellow powder in 95% yield. H NMR (400 MHz, CDCl$_3$) δ (ppm): 2.17 (br s, 6H) 3.91 (br m, 4H), 4.46 (br s, 2H), 6.66-7.13 (br m, 8H). BET surface area=1057 m$^2$ g$^{-1}$, total pore volume=0.75 cm$^3$ g$^{-1}$ at p/p$_o$=0.98, adsorption. TGA analysis: (Nitrogen), initial weight loss due to thermal degradation commences at T$_d$=350° C.

Example 8

Synthesis of Tröger's Base Ladder Polymer 2 (TB-2)

Following the above typical procedure, TB-2 was prepared from 9,10-dichloro-2,6(7)-diaminotriptycene as in 95% yield. $^1$H NMR (400 MHz, CDCl$_3$) δ (ppm): 3.99 (br m, 4H), 4.48 (br s, 2H), 7.01-7.56 (br m, 8H).

Example 9

Synthesis of Tröger's Base Ladder Polymer 3 (TB-3)

Following the above typical procedure, TB-3 was prepared from 9,10-dibromo-2,6(7)-diaminotriptycene in 92% yield. $^1$H NMR (400 MHz, CDCl$_3$) δ (ppm): 4.0 (br m, 4H), 4.48 (br s, 2H), 6.99-7.61 (br m, 8H).

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A composition, comprising:
   a monomer having the following structure:

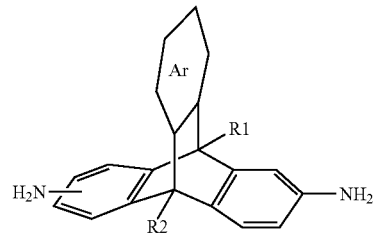

wherein R1 and R2 are independently selected from the group consisting of an aryl group, a linear or branched alkyl group, a halogen and a nitrile group, with the proviso that at least one of R1 and R2 is a halogen and wherein Ar is an unsubstituted aryl group or unsubstituted heteroaryl group.

2. A method of making a monomer comprising:

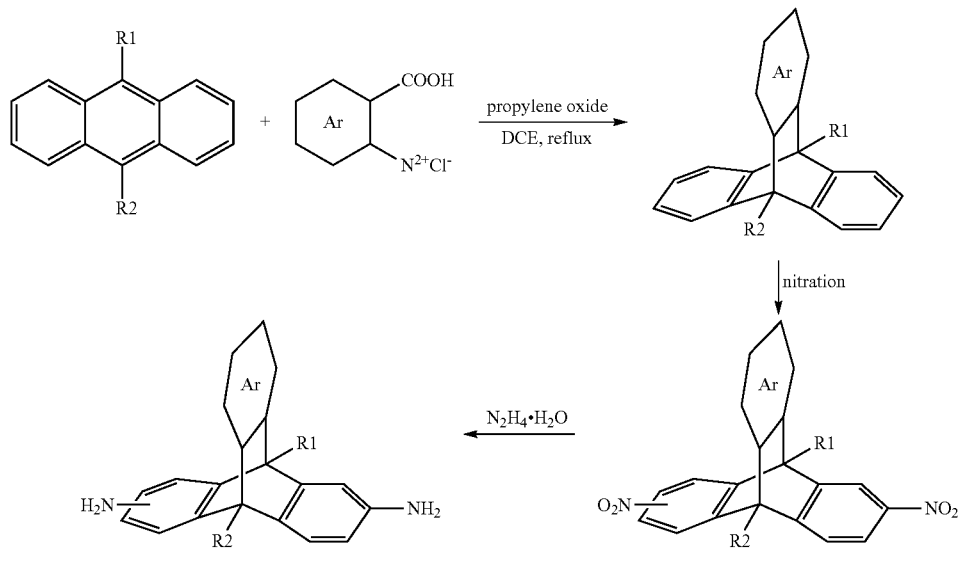

wherein Ar is an unsubstituted aromatic moiety, wherein R1 and R2 are independently selected from the group consisting of an aryl group, a linear or branched alkyl group, a halogen and a nitrile group, with the proviso that at least one of R1 and R2 is a halogen.

3. A composition comprising: a polymer having the following structure:

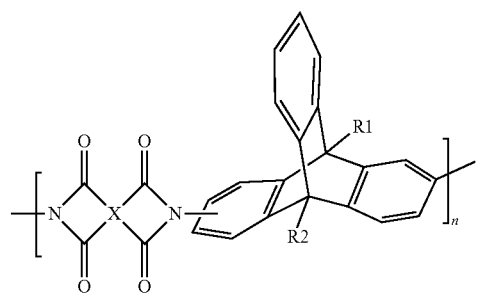

wherein X is a tetravalent radical having an aromatic or aliphatic ring, wherein each of R1 and R2 are independently selected from the group consisting of an aryl group, a linear or branched alkyl group, a halogen and a nitrile group, with the proviso that at least one of R1 and R2 is a halogen, and wherein n is 1 to 10,000.

4. The composition of claim 3, wherein X is:

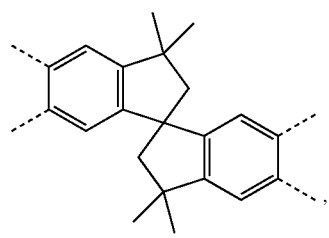

-continued

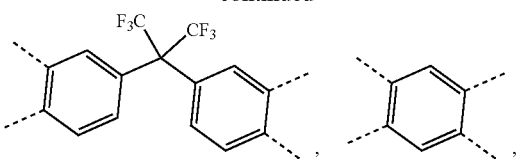

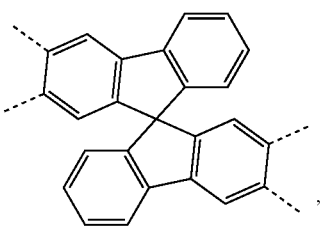

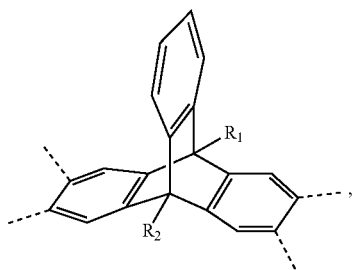

-continued
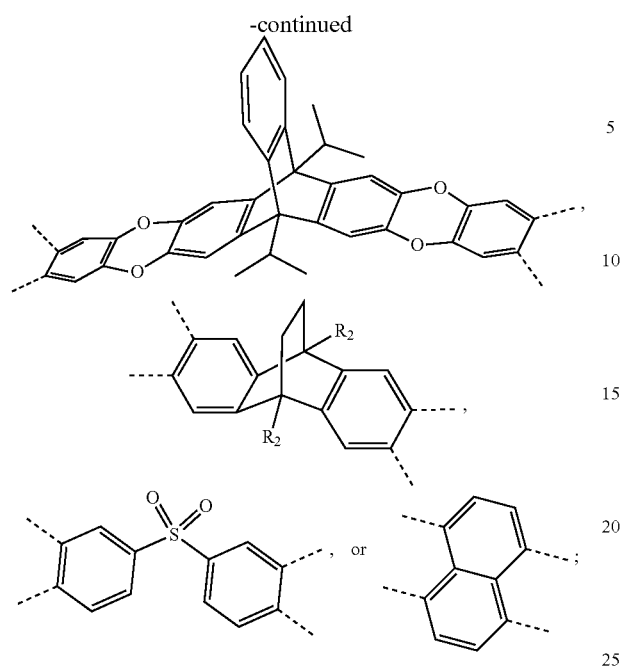
wherein each $R_1$ and $R_2$, as used for the structures of X, is independently selected from the group consisting of H, a halogen, and an alkyl group.
5. A composition comprising: a polymer having the following structure:
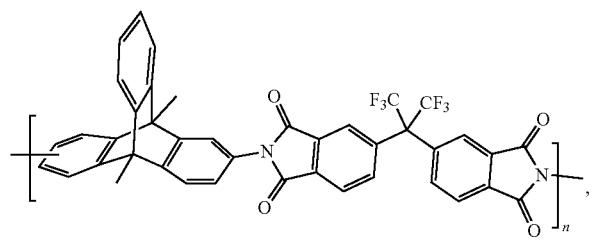
PI-1
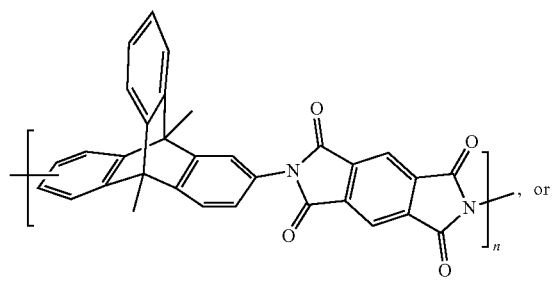
PI-2
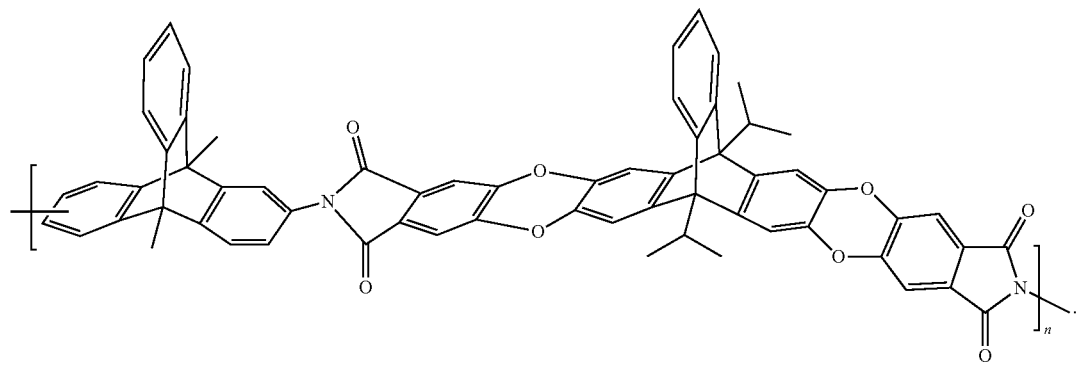
PI-3 wherein Ar is an unsubstituted aromatic moiety, wherein $R_1$ and $R_2$ are independently selected from the group consisting of an aryl group, a linear or branched alkyl group, a halogen and a nitrile group, with the proviso that at least one of R1 and R2 is a halogen and wherein n is 1 to 10,000.

6. A membrane comprising: a polymer of claim 5.

7. A gas separation system comprising: a membrane of claim 6.

8. A membrane comprising: a polymer of claim 3.

9. A gas separation system comprising: a membrane of claim 8.

10. A method of separating a mixture, comprising:
introducing a fluid mixture to a membrane of claim 7 or 9, wherein the mixture includes a first fluid component and a second fluid component that is different than the first fluid component; and
separating the first fluid component from the second fluid component; wherein the first component passes through the membrane and the second component does not substantially pass through the membrane.

11. The method of fluid separation of claim 10, wherein the fluid mixture includes a mixture selected from the group consisting of $O_2/N_2$; $N_2/CH_4$; $H_2/N_2$; $H_2/C_{1+}$ hydrocarbon; $He/C_{1+}$-hydrocarbons; $CO_2/C_{1+}$ hydrocarbons; $CO_2/N_2$; $H_2S/CH_4$; $H_2O/CH_4$ and olefin/paraffin.

12. The polymer of claim 5, wherein at least one of R1 and R2 is chloride.

13. The polymer of claim 12, wherein both R1 and R2 are chloride.

14. The method of claim 10, wherein both R1 and R2 are a halogen.

15. The method of claim 10, wherein the membrane comprises a polymer having the following structure:

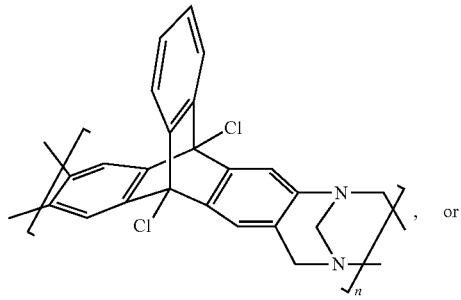

, or

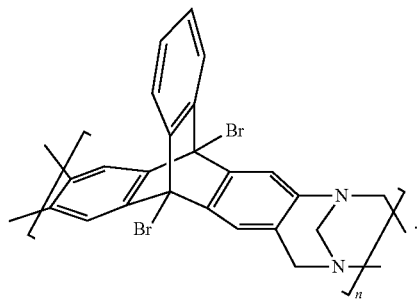

.

wherein n is an integer from 1 to 10,000.

* * * * *